United States Patent
Austin et al.

(10) Patent No.: US 11,602,423 B2
(45) Date of Patent: Mar. 14, 2023

(54) METHOD AND APPARATUS FOR PROVIDING INDICATION OF THE ONCOMING PARTURITION IN LIVESTOCK

(71) Applicant: Moocall Limited, Blackrock (IE)

(72) Inventors: Niall Austin, Birr (IE); Milan Vukajlovic, Belgrade (RS)

(73) Assignee: Moocall Limited, Blackrock (IE)

( * ) Notice: Subject to any disclaimer, the term of this patent is extended or adjusted under 35 U.S.C. 154(b) by 572 days.

(21) Appl. No.: 16/308,205

(22) PCT Filed: Mar. 16, 2017

(86) PCT No.: PCT/EP2017/056317
§ 371 (c)(1),
(2) Date: Dec. 7, 2018

(87) PCT Pub. No.: WO2017/211473
PCT Pub. Date: Dec. 14, 2017

(65) Prior Publication Data
US 2019/0298504 A1    Oct. 3, 2019

(30) Foreign Application Priority Data
Jun. 8, 2016    (GB) ...................................... 1610048

(51) Int. Cl.
*A61D 17/00* (2006.01)
*A61B 5/11* (2006.01)
*A61B 5/00* (2006.01)

(52) U.S. Cl.
CPC .......... *A61D 17/008* (2013.01); *A61B 5/1123* (2013.01); *A61B 5/6813* (2013.01); *A61B 5/6831* (2013.01); *A61B 2503/40* (2013.01)

(58) Field of Classification Search
CPC ... A61D 17/008; A61B 5/1123; A61B 5/6813; A61B 5/6831; A61B 2503/40; A61B 17/00; A01K 29/005
See application file for complete search history.

(56) References Cited

FOREIGN PATENT DOCUMENTS

| EP | 0377343 A1 | 7/1990 |
| GB | 1579807 A | 11/1980 |
| GB | 2257886 A | 1/1993 |
| WO | 2013186235 A1 | 12/2013 |

OTHER PUBLICATIONS

International Search Report issued in International Application No. PCT/EP2017/056317 dated Jun. 8, 2017.

*Primary Examiner* — Patrick Fernandes
(74) *Attorney, Agent, or Firm* — Brian J. Colandreo; Jeffery T. Placker; Holland & Knight LLP

(57) ABSTRACT

This invention relates to a method of providing an indication of the oncoming parturition in livestock and an apparatus for carrying out the method. A tail mounted sensor is mounted on the tail of an animal such as a cow or a horse and the tail mounted sensor detects whether the tail is raised or lowered. Each time that the tail is raised by at least a fixed angle Θ of, say 10°, for a certain period of time $T_1$, the sensor records this as a contraction. The sensor then monitors the number of contractions over a given second period of time, $T_2$. When the number of contractions in the second period of time equal or exceed a certain amount, an alarm is raised. The method and system are such that they can be adjusted for different animals. It is envisaged that less false alarms and less missed births will result as a consequence of this method and apparatus.

15 Claims, 4 Drawing Sheets

METHOD AND APPARATUS FOR PROVIDING INDICATION OF THE ONCOMING PARTURITION IN LIVESTOCK

CROSS-REFERENCE TO RELATED APPLICATIONS

This application is a U.S. National Stage of International Patent Application No. PCT/EP2017/056317, filed 16 Mar. 2017, which claims priority to Great Britain Patent Application No: 1610048.9, filed 8 Jun. 2016, the disclosure of which is incorporated herein by reference in its entirety.

TECHNICAL FIELD

This invention relates to a method and apparatus for providing indication of the oncoming parturition in livestock.

BACKGROUND ART

In order to improve animal welfare and the outcome of labour in livestock, it is known to provide apparatus that monitor the livestock and alert a farmer or responsible individual when the livestock are about to give birth. There are a number of disparate types of monitoring systems known in the art. One such system comprises a video link from a stable where the animal is kept to a remote monitoring station. In this way, the animal may be monitored constantly. Although this system will allow the farmer to detect the oncoming parturition, it requires constant monitoring by the farmer and as such is time consuming to implement. Furthermore, the system is relatively expensive to install and does not cater for animals that may be outside in the field. Therefore, this type of system is typically only used for very high value livestock such as thoroughbred racehorses.

Another system currently available comprises a temperature probe inserted into the animal's birth canal. As the calf enters the birth canal, the temperature probe is expelled from the animal and the resultant drop in temperature is recorded by the probe. This drop in temperature is used to trigger an alert to the farmer to indicate to the farmer that the animal is about to give birth. An example of this type of sensor arrangement is described in UK Patent No. GB1301407 in the name of NDCH & Co. There are however numerous problems with this type system. First of all, the insertion of the device into the animal can cause infection. Secondly, the temperature probe may be uncomfortable for the animal and a source of irritation and distress which is highly undesirable. Thirdly, it is not uncommon for the animal to expel the temperature probe prematurely and as a result, false alarms are commonplace. Furthermore, as the calf is already in the birth canal by the time that the alert is issued to the farmer, the birth is imminent and it is not uncommon for the farmer to miss the birth event.

Another type of system that attempts to address the problem and the shortcomings of the above-mentioned systems relies on monitoring the tail angle of the livestock. It is known that livestock raise their tail for sustained periods when going into and through labour. By monitoring the tail angle, it is possible to predict when the animal is about to give birth. For example, UK Patent No. GB1558330 in the name of Rene Lorette describes a system that monitors the angle of a cow's tail and sounds an alarm if the tail is held in a raised configuration for greater than a predetermined period of time. The period of time does not appear to be specified. Similarly, UK Patent No. GB1579807 in the name of Jean-Paul Begouen describes a system that monitors the angle of a cow's tail and sounds an alarm if the tail is continuously held in a horizontal configuration for approximately 100 seconds. United States Patent No. EP0377343 in the names of Menetrier and Seignot describe a tail mounted sensor that sounds an alarm if the tail has been kept in a raised configuration for an extended period of time, typically between 4 and 12 minutes. Finally, UK Patent Application No. GB2257886 describes a system in which an alert will be generated if the animal's tail is held in a substantially horizontal configuration for a predetermined length of time, preferably of the order of 3 minutes.

Although the above-identified disclosures that operate based on monitoring the length of time that the animal's tail is held in a raised configuration address many of the problems of the other known systems, there are still some shortcomings with these systems. For example, if the time period after which an alarm is raised is set too short, the simple act of the animal urinating or defecating (during which they also raise their tail) can be sufficient to trigger the alarm. In those cases, the farmer will be called out unnecessarily. Conversely, if the time period after which an alarm is raised is set too long, the animal will already be in an advanced stage of labour and the farmer may be too late and miss the birth, defeating the purpose of the system. Furthermore, although there are some similarities, every animal is different and each animal progresses through labour at different rates and what is appropriate for one animal may not be appropriate for another. Therefore, generally speaking, these systems have failed to gain traction in the marketplace.

It is an object of the present invention to provide a method and apparatus for providing indication of the oncoming parturition in livestock that overcome at least some of the problems with the known methods and apparatus and that provide a useful choice to the consumer.

SUMMARY OF INVENTION

According to the invention there is provided a method of providing indication of the oncoming parturition in livestock comprising the steps of:
using a tail-mounted sensor, monitoring the tail movements of the animal and for each time that the animal raises its tail by a predetermined angle, $\theta$, for at least a first predetermined period of time, $T_1$, registering that event as a contraction;
monitoring the number of contractions of the animal over a second predetermined period of time, $T_2$; and
on detecting that there have been a predetermined multiple number, N, of contractions over the second predetermined period of time, $T_2$, so that:

2 minutes $\leq (T_2/N) \leq 6$ minutes, signaling an alert indicating the oncoming parturition of the animal.

By having such a method, it will be possible to more reliably and more accurately predict the imminent birth of an animal and to alert a farmer so that they may be in attendance at the birth. By monitoring the movements of the animal's tail in this manner over a prolonged period of time and determining the number of times that the animal raises their tail by a given amount and for a given period of time over the prolonged monitoring period, the method according to the invention significantly reduces the number of attendances due to false alarms and also reduces the number of missed births. Furthermore, it is possible to tailor the method to the individual animal and the individual farmer's needs.

In one embodiment of the invention there is provided a method in which: 30 minutes≤$T_2$≤50 minutes.

In one embodiment of the invention there is provided a method in which: 35 minutes≤$T_2$≤45 minutes.

In one embodiment of the invention there is provided a method in which $T_2$=40 minutes. 40 minutes has been found to be a particularly suitable time period over which to monitor the movements of the livestock's tail and to alert the farmer if the animal has experienced the predetermined number, N, of contractions over that period of time. This time period is long enough to ensure that a representative sample is taken while at the same time is sufficiently short to avoid missing births of easy calving cow's young, thereby improving the reliability of the method.

In one embodiment of the invention there is provided a method in which: 5≤N≤15.

In one embodiment of the invention there is provided a method in which: 8≤N≤12.

In one embodiment of the invention there is provided a method in which N=10. 10 contractions has been found to be the preferred number of contractions over the time period, $T_2$, to ensure that the animal is indeed in the advanced stages of labour and to ensure that the farmer is not called out prematurely or unnecessarily. This increases the accuracy of the system and method.

In one embodiment of the invention there is provided a method in which: 2 seconds≤$T_1$≤30 seconds.

In one embodiment of the invention there is provided a method in which: 5 seconds≤$T_1$≤15 seconds.

In one embodiment of the invention there is provided a method in which $T_1$=10 seconds. 10 seconds is seen as the preferred time period as it obviates the likelihood of other animal tail movements, such as those experienced while the animal is urinating, defecating or swatting flies, being mistaken for contractions.

In one embodiment of the invention there is provided a method in which $\theta$≥7°.

In one embodiment of the invention there is provided a method in which $\theta$≥10°. 10° is seen as the preferred minimum angle to ensure that the animals tail is in fact being raised.

In one embodiment of the invention there is provided a method in which the step of signaling an alert indicating the oncoming parturition of the animal comprises transmitting a short messaging service (SMS) message to a remote receiver.

In one embodiment of the invention there is provided a method in which the step of monitoring the tail movements of the animal comprises using a constant false alarm rate (CFAR) filter to monitor the tail movements. This is seen as particularly advantageous as the CFAR filter will remove "noise" of regular movements of the animal and its tail, thereby reducing the number of false alarms and improving the accuracy and reliability of the method. In this way, it is possible to provide a variable threshold value to detect a contraction in the animal. This is seen as particularly advantageous as neither the tail angle when the tail is in a normal position nor the tail angle when the tail is in a raised position are considered as constant values and therefore this noise is effectively removed with the use of a CFAR having a variable threshold value.

In one embodiment of the invention there is provided a method in which the step of monitoring the tail movements of the animal comprises using a low pass filter to monitor the tail movements. By using a low pass filter to monitor the tail movements, the movement of the animal and the animal's tail to waive off flies and the like will be effectively removed from consideration and therefore a more reliable method will be provided. In the present embodiment, the low pass filter is effectively the mean value of tail angle taken over a 12 seconds window. This considerably reduces the number of samples required for consideration. If desired, the low pass filter can be removed if an Inertial Measurement Unit (IMU) sensor fusion accelerometer and gyroscope, and, if desired, a magnetometer is provided instead. This is because the sensor fusion will perform the low pass filtering operation. However, the use of an accelerometer with a low pass filter instead of the IMU sensor fusion and gyroscope is believed to extend battery life and therefore is seen as advantageous.

In one embodiment of the invention there is provided a method in which the step of monitoring the number of contractions of the animal over a second predetermined period of time comprises using a leakage accumulator. This is seen as a particularly effective way of carefully monitoring the number of contractions of the animal and correctly identifying when the animal is in fact going through the appropriate stage of labour.

In one embodiment of the invention there is provided an apparatus for providing indication of the oncoming parturition in livestock comprising: a tail-mountable sensor arranged to monitor the tail movements of the animal including means to monitor each time that the animal raises its tail by a predetermined angle, $\theta$, for at least a first predetermined period of time, $T_1$, and register that event as a contraction; means to monitor the number of contractions of the animal over a second predetermined period of time, $T_2$; and means, on detecting that there have been a predetermined number, N, of contractions over the second predetermined period of time, $T_2$, so that $(T_2/N)$≤6 minutes, to signal an alert indicating the oncoming parturition of the animal. Such a sensor will improve the accuracy and reliability of the system and will overcome many of the shortcomings of the known monitoring systems.

In one embodiment of the invention there is provided an apparatus in which: 30 minutes≤$T_2$≤50 minutes; and 5≤N≤15.

In one embodiment of the invention there is provided an apparatus in which $T_2$=40 minutes.

In one embodiment of the invention there is provided an apparatus in which N=10.

In one embodiment of the invention there is provided an apparatus in which the predetermined angle, $\theta$≥10°.

In one embodiment of the invention there is provided an apparatus in which the time, $T_1$≥10 seconds.

In one embodiment of the invention there is provided an apparatus in which the means to monitor the tail movements of the animal comprise a constant false alarm rate (CFAR) filter.

In one embodiment of the invention there is provided an apparatus in which the means to monitor the tail movements of the animal comprise a low pass filter.

In one embodiment of the invention there is provided an apparatus in which the means to monitor the number of contractions of the animal over a second predetermined period of time comprises a leakage accumulator.

In one embodiment of the invention there is provided an apparatus in which the means to signal an alert indicating the oncoming parturition of the animal comprises an SMS transmitter.

In one embodiment of the invention there is provided a method of detecting oncoming parturition in a livestock animal comprising the steps of:

monitoring the tail movements of the animal with a tail mounted sensor and for each time the animal raises its tail by a predetermined angle, θ, for at least a first predetermined period of time, $T_1$, registering that event as a contraction and incrementing the present value, N, of an accumulated events counter each time a contraction is registered;

on the present value, N, of the accumulated events counter reaching a first threshold value, $V_1$, starting a timer of a second period of time, $T_2$;

monitoring the present value, N, of the accumulated events counter for the second period of time $T_2$;

periodically decrementing the present value, N, of the accumulated events counter by a leakage value, $LV_1$; and determining that there is an oncoming parturition in the livestock if the present value, N, of the accumulated events counter reaches a second threshold value $V_2$ during the time period $T_2$.

In one embodiment of the invention there is provided a method of detecting oncoming parturition in livestock in which the step of determining that there is an oncoming parturition in the livestock if the present value, N, of the accumulated events counter reaches a second threshold value $V_2$ during the time period $T_2$ further comprises determining that there is an oncoming parturition in the livestock if the present value, N, of the accumulated events counter reaches a second threshold value $V_2$ during the time period $T_2$ and the present value, N, of the accumulated events counter does not drop below a third threshold value, $V_3$, during the time period $T_2$.

In one embodiment of the invention there is provided a method of detecting oncoming parturition in livestock in which on the present value, N, of the accumulated events counter dropping below the third threshold value, $V_3$, during the time period $T_2$, the method comprises the step of resetting the timer of the second period of time $T_2$.

In one embodiment of the invention there is provided a method of detecting oncoming parturition in livestock in which the method comprises the step of starting to periodically decrement the present value, N, of the accumulated events counter by the leakage value, $LV_1$ if the time since the previous contraction exceeds a third period of time $T_3$.

In one embodiment of the invention there is provided a method of detecting oncoming parturition in livestock in which the first threshold value, $V_1$, is greater than 1.

In one embodiment of the invention there is provided a method of detecting oncoming parturition in livestock in which the second period of time, $T_2$, is of the order of 40 minutes and the second threshold value, $V_2$, is equal to 10.

BRIEF DESCRIPTION OF THE DRAWINGS

The invention will now be more clearly understood from the following description of some embodiments thereof given by way of example only with reference to the accompanying drawings, in which:—

FIG. 3(*b*) is a diagrammatic representation of a cow with a sensor mounted on it's tail and it's tail raised.

DETAILED DESCRIPTION OF THE DRAWINGS

Figure 1:
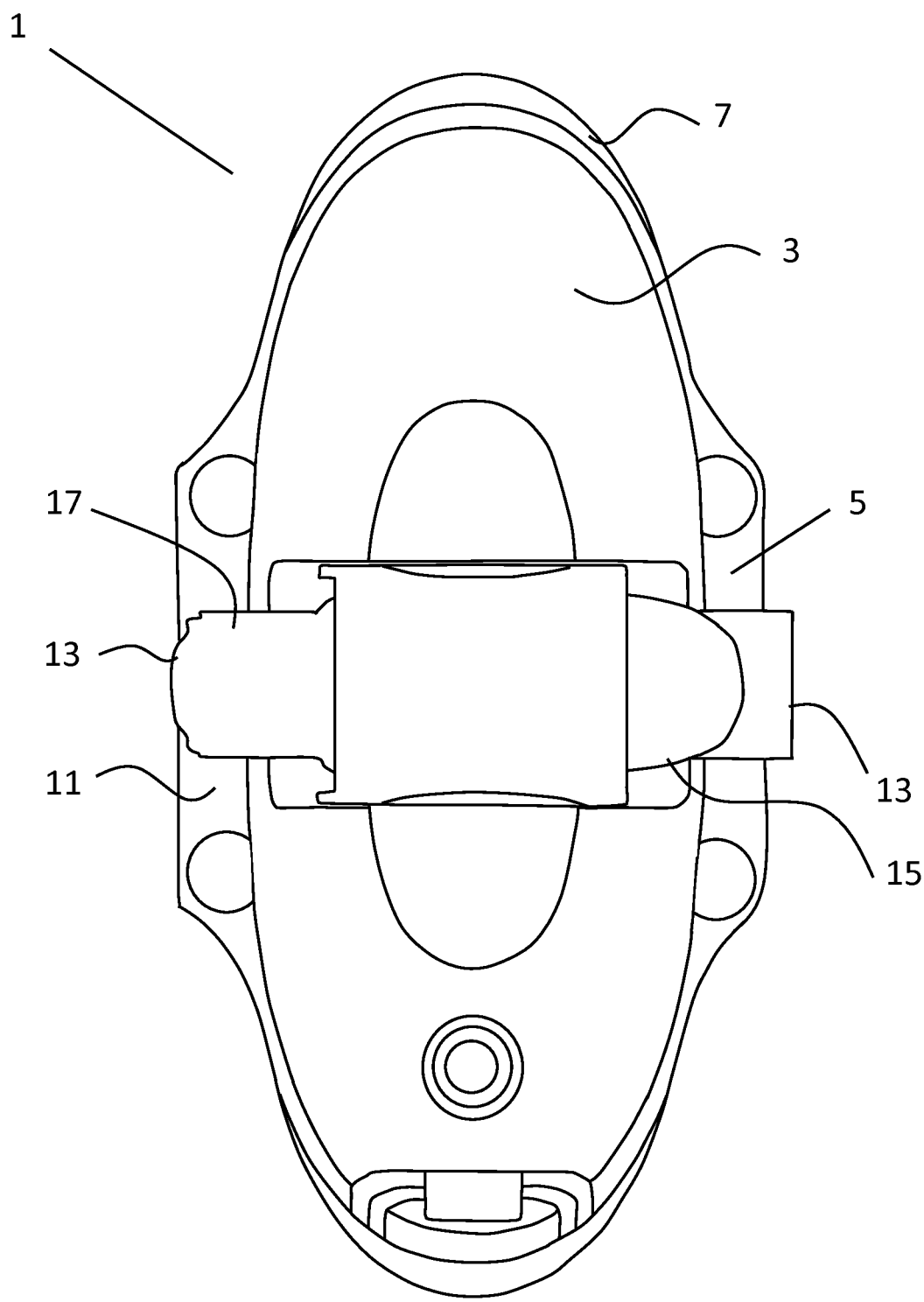
FIG. 1 is a perspective view of a tail-mountable sensor for use in the method according to the invention.

Referring to FIG. 1 there is shown a birthing sensor, indicated generally by the reference numeral 1, for mounting on the tail of a pregnant animal (not shown), the birthing sensor 1 comprising a casing 3 and a strap 5. The birthing sensor 1 further comprises a padding insert 7 provided by way of a sheet of resiliently deformable material. The padding insert 7 provides a secure, non-slip engagement between the tail of the animal and the birthing sensor.

The strap 5 comprises a two part strap including a first part 11 that is formed integrally with the casing 3 and a second, narrower part 13 that extends from the first part 11. The second, narrower part 13 of the strap 5 is connected to the first part 11 of the strap adjacent one of its ends 15 and is dimensioned for insertion into a buckle 15 mounted on the casing. The second part 13 of the strap comprises a toothed strap having a plurality of teeth 17 formed along it length and the buckle 15 and second part of the strap 13 combine to form a ratchet-type securing arrangement in which as the strap 13 is fed through the buckle, the buckle will begin to engage the strap. As the buckle 15 is closed, the buckle will draw the strap 13 tighter around the animal's tail. Internal the casing 3, the birthing sensor has a PCB assembly (not shown) on which various measurement equipment and communication equipment is provided. The measurement equipment includes a constant false alarm rate (CFAR) filter, a low pass filter and a leakage accumulator. An accelerometer such as a three axis accelerometer, a tilt switch, a gyroscope or equivalent device will be provided to determine the tilt angle of the tail.

Figure 2:
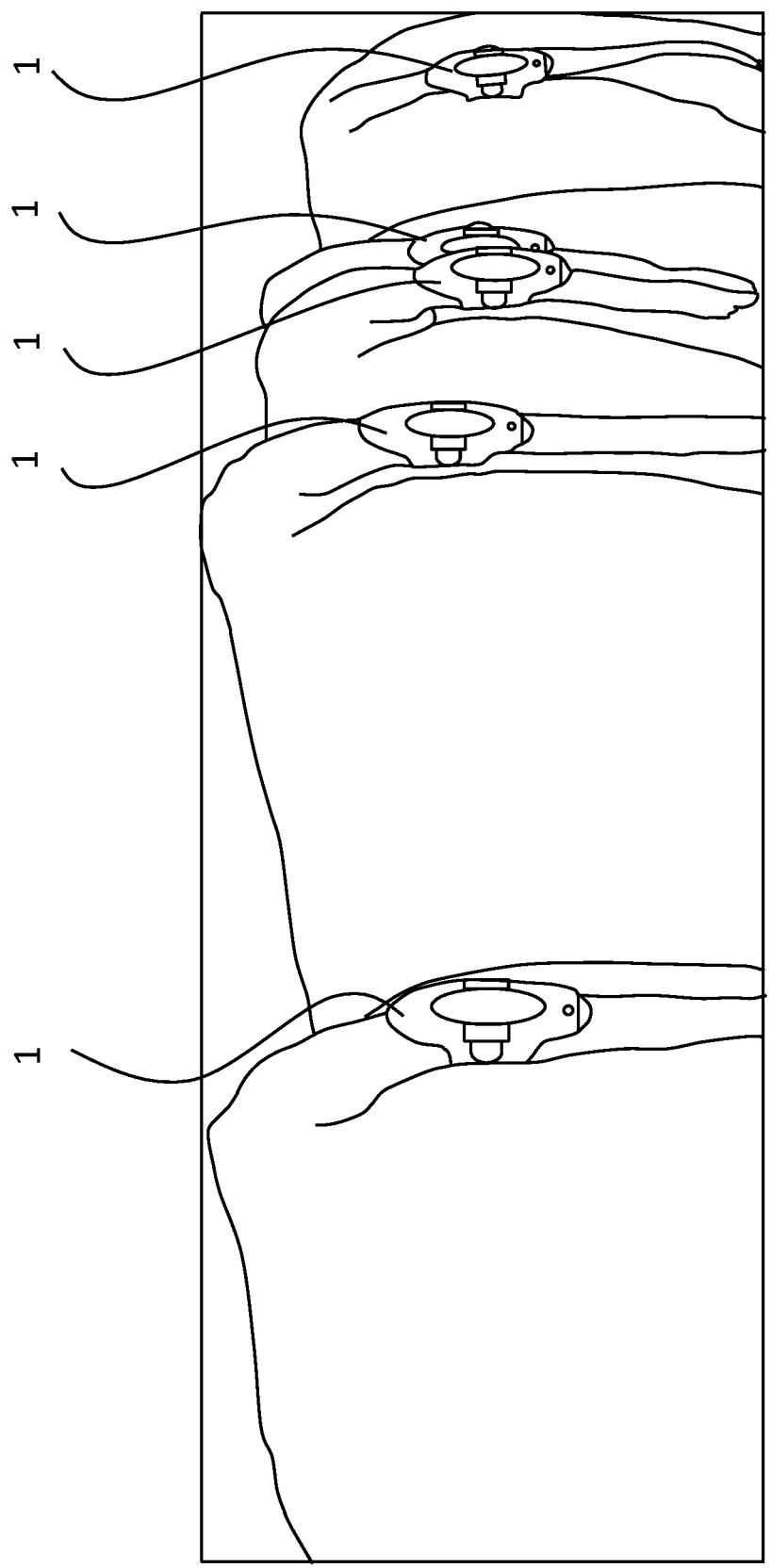
FIG. 2 is a perspective view of a plurality of the sensors, each mounted on the tail of livestock.
Figure 3A:
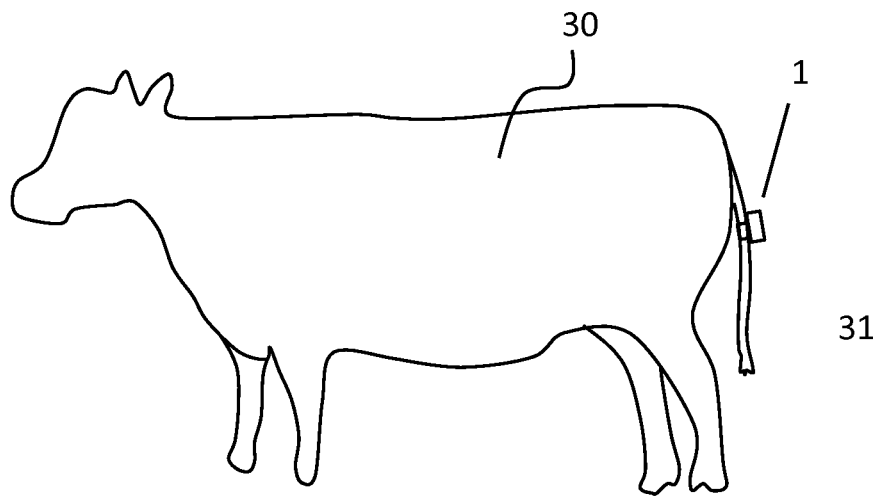
FIG. 3(*a*) is a diagrammatic representation of a cow with a sensor mounted on it's tail and it's tail lowered.
Figure 3B:
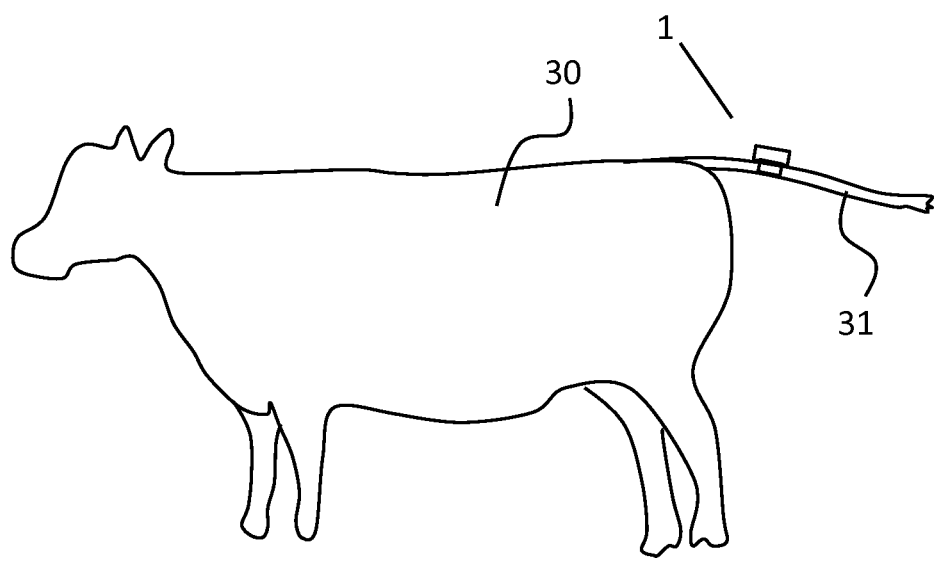

Referring to FIG. 2, there is shown a plurality of sensors 1 for use in the method according to the invention, each of which is mounted on the tail of a cow. Referring to FIGS. 3(*a*) and 3(*b*), there is shown a diagrammatic representation of a cow 30 with it's tail 31 lowered (FIG. 3(*a*)) and a diagrammatic representation of a cow 30 with it's tail 31 raised (FIG. 3(*b*)). As the cow 30 undergoes a contraction, it will lift it's tail 31 from the position shown in FIG. 3(*a*) to the position shown in FIG. 3(*b*).

In use, a sensor 1 is placed on the tail of a cow. The sensor has monitoring equipment therein to monitor the orientation of the sensor on the cow's tail. If the cow raises its tail beyond a predetermined angle, typically of the order of 10° from the vertical (or, more specifically, from the normal resting position which may be offset to the vertical), the sensor will start a timer. If the timer reaches a predetermined time, $T_1$, typically of the order of 10 seconds, and the tail is still raised, the monitoring equipment registers the event as a contraction. If the cow lowers its tail before the timer reaches the predetermined time, the event is not registered as a contraction. Once the tail is lowered, the timer is reset awaiting the next time that the cow's tail is raised. Another contraction will not be registered until the tail has been lowered and the timer has been reset. A CFAR filter and a low pass filter are used to eliminate normal movements of the animal and of the animal's tail to ensure that these are not incorrectly recorded as a contraction.

The monitoring equipment determines the number of contractions over a second period of time, $T_2$ using a leakage accumulator. $T_2$ is effectively a rolling monitoring window, in this case having a duration of 40 minutes. If there are a predetermined number of contractions, N, in this case (N=) 10 contractions over the period $T_2$, an alarm is generated and notified to the farmer (rather than being time periods per se, $T_1$ and $T_2$ may be considered as time thresholds).

Figure 4:
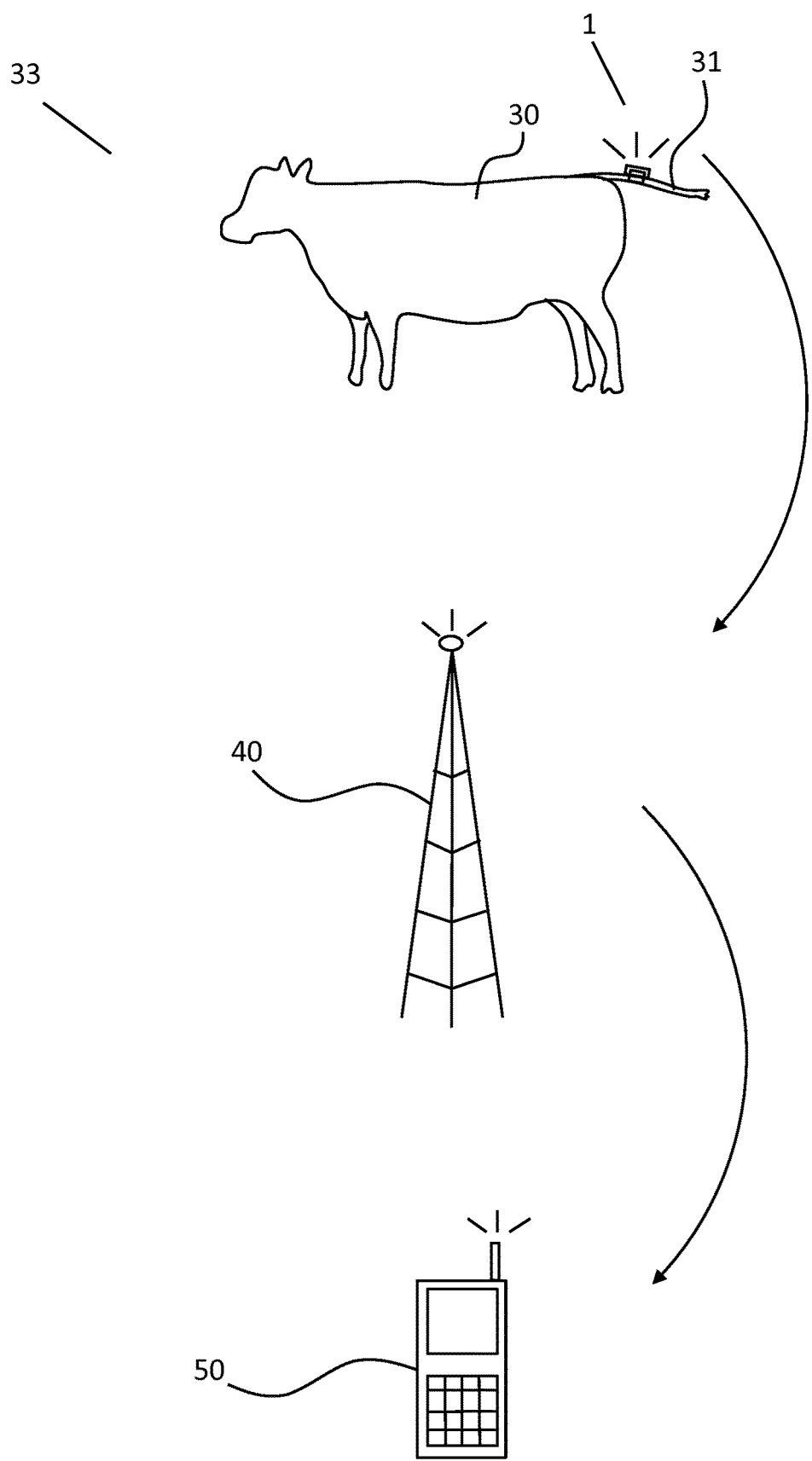
FIG. 4 is a diagrammatic representation of the system in which the method and the birthing sensor according to the invention operate.

Referring to FIG. 4, there is shown a diagrammatic representation of the system 33 in which the method and the birthing sensor 1 according to the invention operate. When the cow has raised its tail by a predetermined amount (e.g. by 10° from the vertical or the normal resting position) for a first predetermined period of time $T_1$ (i.e. 10 seconds) a predetermined number of times (i.e. 10 times) in a set period of time $T_2$ (i.e. 40 minutes), an alarm is raised by the sensor and an SMS alert message is transmitted via the SMS network 40 to the farmers mobile telephone 50. If desired, other communication modes other than SMS could be used to equally good effect.

It has been found that calving can effectively be divided into 3 stages: Stage 1: Uterine contractions begin, restlessness (lasting between 2 to 6 hours); Stage 2: Uterine contractions increase, fetus enters birth canal and at the end calf delivery is completed (lasting between 0.5 to 4 hours); and Stage 3: Afterbirth is expelled.

Stage 1 of calving begins with contraction of the longitudinal and circular muscle fibers of the uterus and ends when the cervix is fully dilated and fetal parts enter the birth canal. Uterine contractions first occur about every 15 minutes, but by the end of stage 1, they occur about every 3 minutes or less. As the first stage progresses, the contractions become strong enough to cause the cow to arch her back and strain slightly. In cattle, the normal duration of stage 1 is 2 to 6 hours, sometimes longer in heifers. The second stage typically lasts from 0.5 to 4 hours. The aim of the present invention is to predict calving around 2 hours prior to the event. Therefore, the present method wishes to detect the transition from Stage 1 to Stage 2.

The 10° angle is also referred to as the offset and is a parameter of the CFAR (Constant False Alarm Detection) filter and it is used to eliminate noise of small regular cow's movements and tail movements. The first predetermined time, $T_1$, is a time threshold to remove acceleration peaks, aggressive movements and short events such as when the sensor hits off a wall or a gate. The number, N, is the minimum number of contractions within one hour (or a given time period) that is required to trigger an SMS alert message. The time $T_2$ was initially set to 1 hour rather than 40 minutes but it was found that because of easy calving cows (which calves herself within 30 minutes) this threshold had to be reduced. If $T_2$ was reduced further, it is envisaged that it would cover more "easy calvings" but it would also potentially cause a lot of false alarms on heifers.

It has been found that the two key parameters in the algorithm are the number, N, of events and the time period $T_2$. N is set to 10 and $T_2$ is set to 40 minutes which is equivalent contractions period of 6 minutes or less and at least 10 contractions. The angle of offset required and the length that the tail has to be inclined can be changed without affecting the efficacy of the method significantly. However, $T_2$ is a key parameter to remove false alarms and in the current solution this value is chosen as a balanced value between false alarms and missed calving events. A higher (i.e. longer) value of $T_2$ will have less false alarms, but more missed easy calving events.

It will be appreciated that the distribution of an animal's contractions over a given period of time is not necessarily uniform, indeed it is highly unlikely for the animal to have contractions that adhere to a strict timing routine. An animal may have a spate of contractions, all very close together in a short period of time and then go for a significant period of time thereafter without experiencing a further contraction. Accordingly, the use of a leakage accumulator greatly facilitates the accurate detection of the birthing event and obviates the possibility of many false alarms.

The leakage accumulator used in the present invention operates in the following manner: the leakage accumulator keeps track of contractions or "events". Each time an "event" occurs, a counter "accumulated events" is incremented by one. When the number of accumulated events equals a first predetermined value, for example 5 (five has been found to be effective for the purposes of the present invention), only then is the timer started to measure time threshold $T_2$. In this way, there is a reasonable degree of certainty that the animal may be going into labour as a number of contraction events have been detected however it is still not known for certain if the animal is going into labour.

The counter "accumulated events" is then periodically decremented by a leakage value. The leakage value is activated six minutes after the detection of a contraction. In other words, the value "accumulated events" will not be reduced for a period of 6 minutes after a contraction but once 6 minutes passes after the contraction, the counter "accumulated events" starts being reduced by the leakage value over time until the next contraction is detected or until the current value of accumulated events is below a certain threshold as a result of lack of contractions. In the present case, once the 6 minute period has passed, the value of "accumulated events" is reduced by the leakage value at intervals determined in part by the sample rate and the current "accumulated events" value. The leakage value is an amount equal to ["Accumulated Events"/(3600*Sample Rate)]. Thereafter, the value of accumulated events can be monitored to see that it reaches a certain level of activity (i.e. that there are a certain number of contractions) and does not fall below a certain threshold of activity (i.e. that the contractions are frequent enough).

For example, if we assume a sample rate of 1 Hz and a current "accumulated events" value of 8 (an even integer value has been chosen simply for the purposes of this example), the leakage value will be 0.00222 (i.e. [8/(3600*1)] and the present value of "accumulated events" (i.e. 8) will be decremented each second by 0.00222. This continues until either the next contraction in which case the current value of "accumulated events" at that time is incremented by one or until the current value of "accumulated events" is less than a given threshold. It will be appreciated that at the rate of decay described above, the current value of "accumulated events" will be equal to zero after one hour if there are no further contractions over that period after the leakage value is applied. If however another contraction is detected, the current value of "accumulated events" will be incremented by one, and after a six minute period, if there are no other contractions, the then current value of accumulated events will be decremented by the then leakage value over time.

One effective way of operating the present invention with the leakage accumulator is as follows: once the value of "accumulated events" is greater than 4.99, the counter $T_2$ is begun. If the current value of "accumulated events" is equal to 10 at a point in time and the value of "accumulated events" has not gone below 3 in the 40 minute period since the value of "accumulated events" was greater than or equal to 5, this is indicative that the animal is in labour and that an alert must be sent out to the farmer. If the value "accumulated events" falls below 3, this shows a lack of activity over a prolonged period and the counter $T_2$ is reset to zero and the process is restarted the next time the value of "accumulated events" is greater than or equal to 4.99. If the value of "accumulated events" is greater than 9 and the counter $T_2$ is greater than 40 minutes, a first calving event is triggered. A message that a calving is imminent may be sent to the farmer at this stage. If, one hour after the first calving event has been triggered the value of "accumulated events" has not dropped below 5, a second calving event is triggered. A message that a calving is imminent may be sent to the farmer at this stage also or instead of the message after the first calving event is triggered.

It will be appreciated that by implementing the invention in this way with the leakage accumulator, it can be determined with a greater degree of probability when the animal is in fact in labour. Furthermore, it will be appreciated that one or more warnings may be sent to the farmer with increasing levels of certainty about whether or not there is a calving likely to take place. Finally, it will be further appreciated that the values described (i.e. the values of 3, 5, 9 and 10 for the "accumulated events" value) and the warnings issued can be carefully chosen and modified to provide the farmer with the desired level or certainty and also to provide greater accuracy over time in the system and method. Indeed, these parameters may be chosen based on the animals characteristics (i.e. type of animal, breed, age, number of previous births, past birthing history) or other conditions. The values used in the present example have been found to be effective for use with cattle in particular.

It will be understood that other values outside of those discussed may also provide useful, albeit suboptimal results. Furthermore, values outside of those discussed, specifically multiples thereof, may also be used to good effect. For example, it is envisaged that the threshold $T_2$ could be set at 80 minutes instead of 40 minutes. The value of N could be increased to 20 or indeed could be maintained at 10 (resulting in $T_2/10=8$). If so, the device will have similar functionality (messages can be sent 40 minutes delayed) which will result in a small number of easy calving events being missed but will still provide an effective, albeit lesser, device. The present claims are intended to cover such scenarios.

Similarly, it would be possible to split the time period or threshold into a number of smaller distinct thresholds that together operate to perform the intention of the invention. For example, it may be possible to send a first warning message after a 20 minute time period in which there were a predetermined number of events (for example 3 or 4). This message alone would provide a large number of false alarms. However, this initial message could be followed up by a second, confirmatory message after 40 minutes. This message could be sent in case there is no activity. In this way, the device will send a message that there is activity (or indeed no activity) and inform the user whether or not the first message was a false alarm. This is also envisaged within the scope of the appended claims.

The ratio $T_2/N$ has been described as important throughout however equivalent or similar ratios that provide similar results are envisaged and these too are envisaged to be within the scope of the appended claims. The value of N, as described above, could be greater than 10, or indeed greater than 15 if desired and appropriate modification could be made to the remaining parameters. Finally, the $T_1$ parameter is preferably set to 10 seconds however alternative values are envisaged and indeed deemed within the scope of the present invention. What is important is that the value of $T_1$ is sufficient to remove acceleration peaks from providing false results. The value for $T_1$ could be longer than 10 seconds if desired.

It will be understood that the present invention extends to software and computer programs running on computer hardware. As such, the present invention may be implemented as a computer program code that, when run on a computer, causes the computer to implement the method. The computer program code may be in object code format, source code format or compiled code format and may be stored on a computer readable medium such as, but not limited to, a CD-ROM, a RAM or other computer memory.

In this specification the terms "comprise, comprises, comprised and comprising" and the terms "include, includes, included and including" are all deemed totally interchangeable and should be afforded the widest possible interpretation.

The invention is not solely limited to the embodiment hereinbefore described and may be varied in both detail and construction within the scope of the appended claims.

The invention claimed is:

1. A method of providing indication of an oncoming parturition in livestock using a tail mounted sensor, the tail mounted sensor comprising a casing and a toothed strap, a buck mounted on the casing for receiving a part of the toothed strap, the buck and the toothed strap combining to form a ratchet-type securing arrangement in which as the toothed strap is fed through the buckle, the buckle will begin to engage the toothed strap and as the buckle is closed, the buckle will draw the strap tighter around the animal's tail, the method comprising the steps of:

using the tail-mounted sensor, monitoring tail movements of an animal and for each time that the animal raises the tail of the animal by a predetermined angle, Θ, for at least a first predetermined period of time, $T_1$, registering that event of the animal raising the tail of the animal by the predetermined angle, Θ, for at least the first predetermined period of time, $T_1$, as a contraction;

monitoring a number of contractions of the animal over a second predetermined period of time, $T_2$; and on detecting that there have been a predetermined multiple number, N, of contractions over the second predetermined period of time, $T_2$, so that:

$$2 \text{ minutes} \leq (T_2/N) \leq 6 \text{ minutes},$$

signalling an alert indicating the oncoming parturition of the animal.

2. The method as claimed in claim 1 in which:

$$30 \text{ minutes} \leq T_2 \leq 50 \text{ minutes}.$$

3. The method as claimed in claim 1 in which:

$$5 \leq N \leq 15.$$

4. The method as claimed in claim 1 in which:

$$2 \text{ seconds} \leq T_1 \leq 30 \text{ seconds}.$$

5. The method as claimed in claim 1 in which Θ≥7°.

6. The method as claimed in claim 1 in which the tail mounted sensor comprises a short messaging service (SMS) transmitter and the step of signaling the alert indicating the oncoming parturition of the animal comprises transmitting a short messaging service (SMS) message to a remote receiver.

7. The method as claimed in claim 1 in which the step of monitoring the tail movements of the animal comprise using a constant false alarm rate (CFAR) filter to monitor the tail movements.

8. The method as claimed in claim 1 in which the step of monitoring the tail movements of the animal comprise using a low pass filter to monitor the tail movements.

9. The method as claimed in claim 1 in which the step of monitoring the number of contractions of the animal over the second predetermined period of time comprise using a leakage accumulator.

10. A method of detecting oncoming parturition in a livestock animal comprising the steps of:
monitoring tail movements of an animal with a tail mounted sensor, the tail mounted sensor comprising a casing and a toothed strap, a buckle mounted on the casing for receiving a part of the toothed strap, the buckle and the toothed strap combining to form a ratchet-type securing arrangement in which as the toothed strap is fed through the buckle, the buckle will begin to engage the toothed strap and as the buckle is closed, the buckle will draw the strap tighter around the animal's tail, and for each time the animal raises the tail of the animal by a predetermined angle, $\Theta$, for at least a first predetermined period of time, $T_1$, registering that event of the animal raising the tail of the animal by the predetermined angle, $\Theta$, for at least the first predetermined period of time, $T_1$, as a contraction and incrementing a present value, N, of an accumulated events counter each time the contraction is registered;
on the present value, N, of the accumulated events counter reaching a first threshold value, $V_1$, starting a timer of a second period of time, $T_2$;
monitoring the present value, N, of the accumulated events counter for the second period of time $T_2$;
periodically decrementing the present value, N, of the accumulated events counter by a leakage value, $LV_1$; and
determining that there is the oncoming parturition in the animal if the present value, N, of the accumulated events counter reaches a second threshold value $V_2$ during the second period of time $T_2$.

11. The method of detecting oncoming parturition in livestock as claimed in claim 10 in which the step of determining that there is the oncoming parturition in the animal if the present value, N, of the accumulated events counter reaches a second threshold value $V_2$ during the second period of time $T_2$ further comprises determining that there is the oncoming parturition in the animal if the present value, N, of the accumulated events counter reaches a second threshold value $V_2$ during the second period of time $T_2$ and the present value, N, of the accumulated events counter does not drop below a third threshold value, $V_3$, during the second period of time $T_2$.

12. The method of detecting oncoming parturition in livestock as claimed in claim 11 in which on the present value, N, of the accumulated events counter dropping below the third threshold value, $V_3$, during the second period of time $T_2$, the method comprises the step of resetting the timer of the second period of time $T_2$.

13. The method of detecting oncoming parturition in livestock as claimed in claim 10 in which the method comprises the step of starting to periodically decrement the present value, N, of the accumulated events counter by the leakage value, $LV_1$ if a time since a previous contraction exceeds a third period of time $T_3$.

14. The method of detecting oncoming parturition in livestock as claimed in claim 10 in which the first threshold value, $V_1$, is greater than 1.

15. The method of detecting oncoming parturition in livestock as claimed in claim 10 in which the second period of time, $T_2$, is of an order of 40 minutes and the second threshold value, $V_2$, is equal to 10.

* * * * *